United States Patent
Lynch

(10) Patent No.: US 6,197,713 B1
(45) Date of Patent: *Mar. 6, 2001

(54) USE OF LEWIS ACIDS FOR THE BREAKDOWN OF GELATINOUS RARE EARTH COMPOUNDS IN HYDROCARBON SOLUTIONS

(75) Inventor: Thomas J. Lynch, Akron, OH (US)

(73) Assignee: Bridgestone Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/994,584

(22) Filed: Dec. 19, 1997

(51) Int. Cl.[7] .............................. B01J 31/00; B01J 37/00; C08F 4/02; C08F 4/60
(52) U.S. Cl. ..................... 502/102; 502/156; 502/169; 502/104
(58) Field of Search .................... 502/102, 154, 502/169

(56) References Cited

U.S. PATENT DOCUMENTS

| | | | |
|---|---|---|---|
| 3,384,678 | * 5/1968 | Stapp | 502/102 |
| 3,554,924 | * 1/1971 | Kittleman et al. | 502/102 |
| 3,641,188 | * 2/1972 | Yoo et al. | 502/102 |
| 3,803,053 | * 4/1974 | Yoo et al. | 502/102 |
| 4,242,232 | 12/1980 | Sylvester et al. | 252/479 C |
| 4,429,089 | 1/1984 | Pedretti et al. | 502/152 |
| 4,461,883 | 7/1984 | Takeuchi et al. | 526/139 |
| 4,619,982 | 10/1986 | Jenkins | 526/164 |
| 4,689,368 | 8/1987 | Jenkins | 525/247 |
| 4,696,984 | 9/1987 | Carbonaro et al. | 526/98 |
| 4,791,086 | * 12/1988 | Yeh et al. | 502/102 |
| 5,021,379 | 6/1991 | Martin et al. | 502/102 |
| 5,064,910 | 11/1991 | Hattori et al. | 526/139 |
| 5,238,895 | * 8/1993 | Machionna et al. | 502/169 |
| 5,360,898 | 11/1994 | Jordaan et al. | 539/16 |
| 5,478,901 | 12/1995 | Jones et al. | 502/152 |
| 5,686,371 | * 11/1997 | Ansell et al. | 502/102 |
| 5,731,253 | * 3/1998 | Sangokoya | 502/102 |
| 5,856,256 | * 1/1999 | Marks et al. | 502/102 |
| 5,858,903 | * 1/1999 | Sylvester et al. | 502/102 |
| 5,877,109 | * 3/1999 | Reichert et al. | 502/103 |
| 5,958,820 | * 9/1999 | Taube et al. | 502/102 |

FOREIGN PATENT DOCUMENTS

| | | | |
|---|---|---|---|
| 572307 | * 6/1962 | (BE) | 502/102 |
| 0 520 732 A1 | 12/1992 | (EP) . | |

OTHER PUBLICATIONS

D.J. Wilson, Polymer, vol. 34, No. 16, pp. 3504–3508, 1993.*
Periodic Table of the Elements with modern group numbering, Alfa/Aesar catalog, 1990.*

* cited by examiner

*Primary Examiner*—Mark L. Bell
*Assistant Examiner*—J. Pasterczyk
(74) *Attorney, Agent, or Firm*—David G. Burleson; Jude Fry

(57) ABSTRACT

The present invention is directed to a process for the preparation of a gel-free hydrocarbon solution containing a lanthanide rare earth series compound by dissolving or synthesizing a lanthanide compound in an inert hydrocarbon solvent with a Lewis acid in an amount sufficient to prevent formation of highly viscous solutions. The present invention is also directed to the use of the gel-free Ln solutions formed by the recited process as co-catalysts for the polymerization of dienes. The Lewis acid is a group 2, 12, 13, 14 or 15 halide or organohalide, or a transition metal halide, excluding aluminum trialkyls.

33 Claims, No Drawings

USE OF LEWIS ACIDS FOR THE BREAKDOWN OF GELATINOUS RARE EARTH COMPOUNDS IN HYDROCARBON SOLUTIONS

FIELD OF THE INVENTION

The present invention relates to the use of certain Lewis acids to breakdown rare earth containing hydrocarbon solutions having high viscosities into low viscosity solutions.

BACKGROUND OF THE INVENTION

It is well known to use catalysts containing a rare earth element for polymerization of a conjugated diene. Polymerization of butadiene by use of rare earth complexes such as neodymium naphthenate has been reported in the "Journal Polymer Science", Vol. 18, 3345 (1980). However, other work in this area is disclosed in U.S. Pat. Nos. 4,242,232 to Sylvester et al, 4,696,984 to Carbonaro et al, and 5,360,898 to Jordaan et al, displaying that neodymium naphthenate can be very difficult to dissolve in a hydrocarbon solvent and produces a gel. Such gels require the use of a relatively large amount of quantities of various viscosity reducing additives, generally in an amount exceeding two moles of additive per each mole of rare earth complex. In said literature reference, polymerization of butadiene is displayed using a ternary catalyst consisting of $NdCl_3$, an alcohol and $Al(C_2H_5)_3$. However, when a catalyst system consisting of this combination is used for polymerization many problems arise because $NdCl_3$ is solid and insoluble in a hydrocarbon solvent and the resulting catalyst component is heterogeneous. Heterogeneous catalysts are disadvantageous for use in industrial operations. Furthermore, catalyst systems consisting of the combination described above have defects, for example, low polymerization activity.

Additionally, such catalysts when treated with viscosity reducing additives are disadvantageous for industrial use for a variety of other reasons. For example, the use of ethers can reduce the stereospecificity of the catalyst. The use of trialkylaluminum compounds can cause the molecular weight distribution to broaden and its molecular weight to decrease. The use of protic viscosity reducing agents can result in the need for more cocatalyst in some polymerizations, thereby raising the cost of catalyst. Finally, the introduction of certain types of viscosity reducing additives can complicate other types of polymerizations if the additives become incorporated into the facilities solvent stream.

The object of this invention is to overcome these disadvantages and to eliminate or reduce the high viscosities occurring upon the mixture of a rare earth complex in a hydrocarbon solvent.

SUMMARY OF THE INVENTION

The present invention relates to a process for the preparation of a non-viscous hydrocarbon solution containing a lanthanide rare earth series compound by dissolving a lanthanide compound in an inert hydrocarbon solvent with a Lewis acid, the Lewis acid being present in an amount sufficient to prevent gel-like formation of highly viscous solutions of the Ln compound when the lanthanum compound is dissolved in the inert hydrocarbon. The Lewis acid is preferably an organometallic halide of a metal in the main group 2, 12, 13 and 14 groups of the Periodic System or a halide of an element of main groups 2, 12, 13, 14 and 15 groups or a transition metal of the Periodic System. Hydrocarbon soluble Lewis acids are the most preferred. The present invention also relates to the non-viscous lanthanide solutions formed by the process.

DESCRIPTION OF THE INVENTION

According to this invention, there is provided a process for reducing the viscosity of a gel-like solution containing a lanthanide rare earth compound by contacting the gel-like solution with a Lewis acid thereby eliminating or reducing the high viscosities. This invention also provides a process for the preparation of a non-viscous solution during the direct synthesis of a lanthanide rare earth series compound in an inert solvent by the addition of a Lewis acid in an amount sufficient to prevent formation of a highly viscous Ln compound and to form a solution having a Brookfield viscosity of less than 1000 centipoise (cps) after treatment with the Lewis acid. The lanthanide rare earth solutions to be treated in accordance with the process of the present invention are normally used in the polymerization of conjugated dienes, and form highly viscous solutions when added to solvents, such as aliphatic hydrocarbons, cycloaliphatic hydrocarbons and aromatic hydrocarbons, preferably hexane. The lanthanide rare earth compounds to be treated are any complexes of a metal belonging to the series of the lanthanides having an atomic number of 57 to 71, in which a ligand is directly bound to the metal and is a monovalent and monodentate organic radical including but not limited to: ($-R^1CO_2$), ($-OR^1$), ($-NR^1R^2$), ($-SR^1$), ($-OPO(OR^2)$), ($-OSO_2(R)$) and ($-PR^1R^2$) wherein R, $R^1$ and $R^2$ are independently selected from alkyl, cycloalkyl and aryl hydrocarbon substituents having 1 to 20 carbon atoms. Suitable lanthanum rare earth compounds to be treated are represented by the following structures: $Ln(R^1CO_2)_3$, $Ln(OR^1)_3$, $Ln(NR^1R^2)_3$, $Ln(SR^1)_3$, $Ln(-OPO(OR)_2)_3$, $Ln(-OSO_2(R))_3$ and $Ln(PR^1R^2)_3$ wherein Ln is a rare earth element in the lanthanide series having an atomic number of 57 to 71 and R, $R^1$ and $R^2$ are independently selected from alkyl, cycloalkyl and aryl hydrocarbon substituents having 1 to 20 carbon atoms.

Ln is a rare earth element in the lanthanide series having an atomic number of 57 to 71; lanthanum, cerium, praseodymium, neodymium and gadolinium are preferred, and neodymium is particularly preferable. The Ln may be a mixture of two or more rare earth elements.

The following are typical examples of rare earth compounds that form highly viscous solutions upon addition to certain solvents or upon preparation in solvents: lanthanum tris[bis(2-ethylhexyl)phosphate] and neodymium tris(2-ethyl hexanoate).

The Lewis acids used to reduce the viscosity of the gel-like rare earth compound solutions, are metal halides including transition metal halides such as $TiCl_4$, $VCl_3$, and the like; and organometallic halides in which the metal atom belongs to the 2, 12, 13 and 14 groups of the Periodic System as well as halides of the elements of 2, 12, 13, 14 and 15 groups of the Periodic System.
methyl aluminum dichloride,
methyl aluminum dibromide,
ethyl aluminum dichloride,
butyl aluminum dibromide,
butyl aluminum dichloride,
dimethyl aluminum bromide,
dimethyl aluminum chloride,
diethyl aluminum bromide,
diethyl aluminum chloride,
dibutyl aluminum bromide, dibutyl aluminum chloride,
methyl aluminum sesquibromide,
methyl aluminum sesquichloride,
ethyl aluminum sesquibromide,
ethyl aluminum sesquichloride,
dibutyl tin dichloride,
aluminum tribromide,
antimony trichloride,
antimony pentachloride,
phosphorus trichloride,
phosphorus pentachloride
boron tribromide
zinc dichloride
magnesium dichloride
magnesium dibromide.n $Et_2O$ and
tin tetrachloride.

The following are preferred Lewis acids for use in preventing gel formation in the solution: zinc dichloride, boron tribromide, tin tetrachloride and hydrocarbon soluble metal halides.

A solution of a gel-free Ln compound may be prepared by swelling/dissolving the Ln compound in an inert solvent and then adding the Lewis acid. Aliphatic, cycloaliphatic and aromatic solvents are suitable for this purpose, including but not limited to: pentane, hexane, heptane, cyclohexane, benzene, and toluene. The quantity of Lewis acid, used in eliminating or reducing the high viscosities normally occurring in a Ln compound in a hydrocarbon solvent, may vary within wide limits. The molar ratio of Lewis acid to Ln is preferably in the range of from 0.005:1 to 5:1, most preferably from 0.05:1 to 0.5:1 and is generally sufficient to prevent gel formation in the Ln solution from which a catalyst may be derived, the advantageous properties of the resulting catalyst being in no way reduced. In accordance with the present invention the viscosity of the viscous solution of Ln compound in a hydrocarbon solvent to be treated or in an untreated state is at least 1000 centipoise. After treatment with a Lewis acid, the Ln compound in a hydrocarbon solvent possesses a viscosity of less than 1000 centipoise.

The non-viscous, gel-free Ln solutions are then suitable for use with other activating catalyst components such as an organic aluminum or magnesium compound, typically represented by Al $R^2$—$R^3R^4$ or Mg $R^2R^3$ wherein $R^2$, $R^3$ and $R^4$, which may be identical or different, represent hydrogen atoms or hydrocarbon substituents having 1 to 8 carbon atoms, excluding the case where $R^2$, $R^3$ and $R^4$ are hydrogen atoms at the same time, in the production of a conjugated diene polymer, characterized by polymerizing at least one conjugated diene.

The temperature range to form the low viscosity Ln containing solution with the Lewis acid may vary within a wide range and is most preferably in the range of from −30° to +50° C., in particular from 0° to 40° C. It is generally limited by the melting point or boiling point of the solvent.

For a given Ln compound, such as $Ln(R^1CO_2)_3$, the time required to form the catalyst component free from gel depends on the nature and quantity of the solvent used, the nature and quantity of the Lewis acid and the temperature. Exact figures therefore cannot be given but it will be seen from the Examples that de-gelled solution generally takes place within a short time.

The molar ratio of catalyst components used in the polymerization of conjugated dienes may vary within wide limits. The molar ratio of the Lewis acid modified Ln catalyst components (component A) to the activating catalysts (component B), such as Al $R^2R^3R^4$ or Mg $R^2R^3$ is in the range of from 1:2 to 1:100, preferably from 1:2 to 1:40 and most preferably from 1:3 to 1:35.

To prepare the catalyst, the solution of components A and B are mixed in any desired sequence in a suitable inert solvent with stirring. The same solvent as that used for the polymerization of the diene may be used for preparation of the catalyst. The temperature at which preparation of the catalyst is carried out may vary within a wide range and is generally limited by the melting point and boiling point of the solvent used. Temperatures ranging from −30° to 300° C., for example, are suitable. Preparation of the catalyst may be carried out separately or, preferably, by the addition and mixing of catalyst component A and B with the polymerization reaction mixture. If desired, components A and B may be mixed together before they are added to the polymerization mixture. It is immaterial whether the diene which is to be polymerized is added before or after the catalyst components or whether the diene is added between the addition of one and the other catalyst component.

The catalyst is highly active and very small quantities are therefore sufficient to produce a catalytic effect. For 100 grams of conjugated diene monomer, from 0.01 to 3 mMol, preferably from 0.01 to 1.0 mMol, of Ln compound catalyst in component A are generally used.

The polymerization of the diene is carried out in organic solvents which must be inert towards the catalyst system used. Suitable solvents include e.g. aromatic, aliphatic and cycloaliphatic hydrocarbons such as benzene, toluene, pentane, n-hexane, iso-hexane, heptane and cyclohexane.

Polymerization with the catalyst according to the invention may be carried out either continuously or batch-wise. It is carried out at a temperature in the range of from 0° to 120° C., preferably from 40° to 100° C. As conjugated dienes; butadiene, isoprene, pentadiene-1.3 and 2.3-dimethylbutadiene, preferably butadiene are useful in the present invention.

In one common method of carrying out the process, components A and B are added to a mixture of 100 parts by weight of solvent and 5 to 40 parts by weight, preferably 0 to 30 parts by weight of butadiene. When 0.16 mMol parts per hundred grams (phg) butadiene of the Ln solution is used, and a polymerization temperature of about 50 to 65° C. is employed, polymerization conversion rates of more than 90% are obtained after reaction times ranging from 2 to 20 hours.

When the desired degree of conversion has been reached, the catalyst is inactivated by the addition of small quantities of, for example, water, carboxylic acids or alcohols.

The usual stabilizers are added to the polymer solution in the usual quantities before the polymer is worked up. The stabilizers used may include, for example, sterically hindered phenols or aromatic amines such as 2,6-di-tert.-butyl-4-methyl phenol.

The polymer is isolated by concentration of the polymer solution by evaporation, precipitation with a non-solvent such as methanol, ethanol or acetone or, preferably steam distillation of the solvent. Drying is carried out by the usual methods, e.g. in a drying cupboard or screw drier.

Both high cis- and high trans- polybutadienes are prepared using the low viscosity Ln solutions of the present invention as part of the catalyst systems. These modified catalyst have the advantage that they perform equally well to comparable known catalysts for preparing either high trans or high cis-polybutadienes.

The invention is described in more detail with the aid of the following examples, in which the percentages are by weight, however ratio of compounds such as catalyst components are in molar ratios.

Catalyst Preparation and Viscosity Measurements

These examples illustrate the effect that small quantities of a Lewis acid can have on the viscosity of rare earth salt/hydrocarbon solutions.

EXAMPLES 1 TO 4

A 3-neck, 3 liter, round bottom flask was fitted with a Dean Stark trap, condenser, and a mechanical Stirrer. Lanthanum oxide (48.9 g, 0.15 mol) was added to the flask followed by the addition of bis(2-ethylhexyl)hydrogen phosphate (302 g, 0.936 mol). This slurry was further diluted with hexane (1.4 liter) and water (50 mL). The solution was heated and allowed to reflux until a clear, light yellow solution had formed. The water was removed by azeotropic distillation. A 500 ml portion, Example 1 (comparative) of the resulting viscous solution was transferred into a 600 ML beaker. The viscosity of this portion of the viscous solution was measured using a Brookfield viscometer and is displayed in Table 1 as Example 1. As Example 2, tin tetrachloride (22 ml, 1.0 Normal Cl in hexane) was added to the remaining solution. The gelatinous consistency of the solution dissipated over a period of minutes. An aliquot of this solution (15 ml) was removed and the viscosity was measured in a Brookfield viscometer fitted with a small sample adapter and is displayed in Table 1 as Example 2. Additional tin tetrachloride (11 ml, 1.0 Normal Cl in hexane) was added to the remaining solution (Example 3). Again, an aliquot (15 ml) was removed and the viscosity measured and is displayed in Table 1 as Example 3. A final portion of $SnCl_4$ (11 ml, 1.0 Normal Cl in hexane) was added to the remaining solution (Example 4) and the resulting viscosity was measured and is displayed in Table 1 as Example 4.

TABLE 1

| Example No. | Catalyst Concentration (mol/liter) | $SnCl_4$/La (molar ratio) | Viscosity (cps) |
| --- | --- | --- | --- |
| 1 | 0.174 | 0 | >90,000 |
| 2 | 0.174 | 0.025 | 204 |
| 3 | 0.174 | 0.038 | 73 |
| 4 | 0.174 | 0.050 | 28 |

It is noted that shear bands developed in the original, untreated solution, Example 1, during the viscosity measurement. In addition, the spindle appeared to bore a hole in the solution. Thus an accurate stable measurement of this gelantinous solution could not be obtained; however, all of the values obtained were in excess of ninety thousand centipoise.

EXAMPLES 5 TO 7

(2-Ethyl)hexanoic acid (81 g) and neodymium acetate monohydrate (28.6 g) were added to a 500 mL round bottom flask. The flask was heated to 120° C. until the slurry developed into a clear solution. The flask was then attached to a distillation assembly. The solution was heated to 150° C. while applying vacuum (0.07 mm). This process was continued until distillation of the excess acid ceased. The yield was 45.5 g of a waxy solid.

The waxy solid was transferred to a 2 liter round bottom flask and dry cyclohexane (615 g) was added. After 24 hours, a clear, light purple, gelatinous solution was obtained. As Example 5, a portion of this solution (343 g) was transferred into a 600 ml beaker and the viscosity of this removed portion was measured and is displayed in Table 2 as Example 5. In Example 6, tin tetrachloride (0.2 ml) was added to the remaining solution and a large and rapid drop in viscosity was observed. An aliquot (16 ml) of this solution was removed and the viscosity of the removed solution was measured and is displayed in Table 2 as Example 6. Finally, tin tetrachloride (0.1 ml) was added to 211 g of the remaining solution. An aliquot (16 ml) of this solution was removed and the viscosity was measured and is displayed in Table 2 as Example 7.

TABLE 2

| Example No. | Catalyst Concentration (mol/liter) | $SnCl_4$/La (molar ratio) | Viscosity (cps) |
| --- | --- | --- | --- |
| 5 | 0.1 | 0 | 600,000 |
| 6 | 0.1 | 0.05 | 705 |
| 7 | 0.1 | 0.08 | 104 |

Polymerization

These following examples demonstrate that there is no detrimental effect of small quantities of Lewis acids on the ability of these compounds to act as cocatalysts in the stereospecific polymerization of dienes.

EXAMPLES 8 TO 11

An oven dried, 750 ml beverage bottle was capped with a crown cap and butyl rubber liner. The bottle was cooled under a stream of dry nitrogen. The bottle was then charged with 230 grams of a 25% by weight solution of butadiene in a dry hexane solution. Next, the bottle was charged with 2.1 ml of lanthanide tris[bis(2ethylhexyl)phosphate] as prepared in Example 4. Finally, 1.18 ml of dibutuylmagnesium (1.0 molar in heptane) was added to the bottle. The polymerization was performed in a 65° C. water bath for 2 hours. A white plastic polybutadiene was recovered by allowing the solvent to evaporate. The molar ratios of catalyst components and Lewis acid polymerization (Pmz) reaction conditions and the resulting properties of the polybutadiene of this polymerization are displayed in Table 3 Example 8).

In Examples 9, 10 and 11, additional catalyst solutions were prepared and used to polymerize butadiene in a manner similar to that described above in Example 8. The polymerization (Pmz) reaction conditions and the resulting properties of the polybutadiene of these polymerizations are also displayed in Table 3. The results of all of these polymerizations clearly indicate that the effectiveness and the nature of the catalyst does not change when a Lewis acid is used to modify the viscosity of the rare earth salt/hexane solution.

TABLE 3

| Exam. No. | Ln* (mMol phgBd) | Mg/La | Lewis Acid/La | Pmz Temp. (° C.) | Pmz Time (hrs) | Yield (%) | $M_n$ (kg/mol) | $M_w$/$M_n$ | $T_m$ (1) (° C.) | $T_m$ (2) (° C.) |
| --- | --- | --- | --- | --- | --- | --- | --- | --- | --- | --- |
| | | | | $SnCl_4$/La | | | | | | |
| 8 | 0.65 | 3.2 | 0.05 | 65 | 2.0 | 100 | 39 | 1.17 | 49 | 98 |
| 9** | 0.16 | 5 | 0.04 | 65 | 3.5 | 89 | 89 | 1.47 | 47 | 96 |

TABLE 3-continued

| Exam. No. | Ln* (mMol phgBd) | Mg/ La | Lewis Acid/ La | Pmz Temp. (° C.) | Pmz Time (hrs) | Yield (%) | $M_n$ (kg/mol) | $M_w/M_n$ | $T_m$ (1) (° C.) | $T_m$ (2) (° C.) |
|---|---|---|---|---|---|---|---|---|---|---|
| | | | | $BBr_3$/La | | | | | | |
| 10 | 0.16 | 7 | 0 | 50 | 16.5 | 100 | 127 | 1.35 | 47 | 99 |
| 11 | 0.16 | 7 | 0.05 | 50 | 16.5 | 99 | 131 | 1.35 | 47 | 99 |

*mmol La/100 g Butadiene
**microstructure: trans = 93%, vinyl = 5%

EXAMPLES 12 AND 13

An (2-ethyl)hexanoic acid and neodymium acetate monohydrate catalyst solution (0.07 M in Nd, $SnCl_4$/Nd=0.07) was prepared in a manner similar to that described above (Examples 5 to 7). The viscosity of the solution was 28 cps. This solution was used to polymerize butadiene as described below.

An oven dried 750 ml beverage bottle was capped with a crown cap and butyl rubber liner. The bottle was cooled under a stream of dry nitrogen. The bottle was then charged with 200 grams of a dry hexane solution containing 23.6 wt % of butadiene. This was followed by additional dry hexane (203 g). The neodymium carboxylate solution (1.41 mL) was then added to the butadiene solution. This was followed by the addition of triisobutylaluminum (4.92 mL, 0.68M in hexane) and diethylaluminum chloride (0.3 ml, 1.0 molar solution in hexane). The polymerization was allowed to proceed in a 50° C. water bath for 2 hours. The solvent was removed in a vacuum oven (50 ° C.). The results of this polymerization are displayed as Example 12 in Table 4.

In Example 13 polymerization was carried in a manner similar to that described for Example 12 except a nonmodified solution of neodymium neodecanoate was used. The results of this polymerization are displayed in Table 4.

TABLE 4

| Example | Yield (%) | $M_w$ (kg/mol) | $M_w/M_n$ | 1,4-cis (%) | 1,2-vinyl (%) | $T_m$ (° C.) | $T_g$ (° C.) |
|---|---|---|---|---|---|---|---|
| 12 | 99 | 282 | 2.64 | 96 | 2 | −3 | −104 |
| 13 | 98 | 284 | 2.40 | | | −4 | −104 |

EXAMPLES 14 TO 16

The effect of other Lewis acids on the gelatinous state of lanthanum tris[bis(2-ethylhexyl)phosphate] in hexane was tested. The conditions used to test these Lewis acids and the observed effect on the solution are summarized in Table 5.

TABLE 5

| Ex. | Lewis Acid | Lewis Acid/La | Effect on Viscosity | Comments |
|---|---|---|---|---|
| 14 | $ZnCl_2$ (1.0M in $Et_2O$) | 0.1 | Very Effective | Similar to effect of $SnCl_4$ |
| 15 | $MgCl_2$ (anhydrous) | 0.5 | Effective | Added as solid. Heat solution/solid for 5 hours in 50° C. water bath. The $MgCl_2$ did not completely dissolve |
| 16 | $MgBr_2.nEt_2O$ | 0.3 | Effective | Treated as with $MgCl_2$. Observation was the same for $MgCl_2$. |

We claim:

1. A gel-free solution consisting essentially of: a mixture of at least one lanthanide series compound having at least one rare earth element in the lanthanide series, an inert solvent, and a Lewis acid, the Lewis acid selected from the group consisting of a transition metal halide, an organometallic halide whose metal is of group 2, 12, 13 and 14 of the Periodic System, and a halide of an element of group 2, 12, 13, 14 and 15 of the Periodic System, the Lewis acid being present in an amount sufficient to prevent gel formation of the at least one lanthanide series compound when mixed with the inert solvent.

2. The solution according to claim 1, wherein the at least one rare earth element in the lanthanide series is lanthanum, cerium, praseodymium, neodymium, or mixtures thereof.

3. The solution according to claim 1, wherein the at least one rare earth element in the lanthanide series is a mixture of rare earth elements with atomic numbers from 57 to 71.

4. The solution according to claim 1, wherein the at least one rare earth element in the lanthanide series is a mixture of rare earth elements containing at least 10% by weight of at least one of lanthanum, cerium, praseodymium, or neodymium.

5. The solution according to claim 1, wherein the inert solvent comprises at least one of an aliphatic, cycloaliphatic, or aromatic solvent.

6. The solution according to claim 1, wherein the inert solvent comprises at least one of pentane, hexane, heptane, cyclohexane, benzene, or toluene.

7. The solution according to claim 1, wherein the molar ratio of Lewis acid to the at least one lanthanide series compound is in the range of from 0.005:1 to 5:1.

8. The solution according to claim 1, wherein the molar ratio of Lewis acid to the at least one lanthanide series compound is in the range of 0.05:1 to 0.5:1.

9. The solution according to claim 1, wherein the at least one lanthanide series compound is represented by a formula selected from the group consisting of $Ln(R^1CO_2)_3$, $Ln(OR^1)_3$, $Ln(NR^1R^2)_3$, $Ln(-OPO(OR)_2$, $Ln(-OSO_2(R))_3$, $Ln(SR^1)_3$, and $Ln(PR^1R^2)_3$, wherein Ln is a rare earth element in the lanthanide series having an atomic number of 57 to 71 and R, $R^1$, and $R^2$ are independently selected from alkyl, cycloalkyl and aryl hydrocarbon substituents having 1 to 20 carbon atoms.

10. The solution according to claim 1, wherein the Lewis acid is $BBr_3$, $SnCl_4$, $ZnCl_2$, $MgCl_2$, or $MgBr_2.n$ $Et_2O$.

11. A process for preparing a gel-free catalyst solution consisting essentially of the steps of: dissolving at least one lanthanide series compound having at least one rare earth element in the lanthanide series in an inert solvent by the addition of a Lewis acid selected from the group consisting of a transition metal halide, an organometallic halide whose metal is of group 2, 12, 13 and 14 of the Periodic System, and a halide of an element of group 2, 12, 13, 14 and 15 of the Periodic System, the Lewis acid being present in an amount sufficient to prevent gel formation of the at least one lanthanide series compound when dissolved in the inert solvent; and optionally, adding an organic magnesium compound to the solution, the organic magnesium compound being of the formula $MgR^2R^3$ wherein $R^2$ and $R^3$ are the same or different and are hydrogen atoms or hydrocarbon substituents having 1 to 8 carbon atoms, excluding the case where $R^2$ and $R^3$ are both hydrogen atoms.

12. The process according to claim 11, wherein the at least one rare earth element in the lanthanide series comprises lanthanum, cerium, praseodymium, neodymium, or mixtures thereof.

13. The process according to claim 11, wherein the at least one rare earth element in the lanthanide series is a mixture of rare earth elements with atomic numbers from 57 to 71.

14. The process according to claim 11, wherein the at least one rare earth element in the lanthanide series is a mixture of rare earth elements containing at least 10% by weight of at least one of lanthanum, cerium, praseodymium, or neodymium.

15. The process according to claim 11, wherein the inert solvent comprises at least one of an aliphatic, cycloaliphatic, or aromatic solvent.

16. The process according to claim 11, wherein the inert solvent comprises at least one of pentane, hexane, heptane, cyclohexane, benzene, or toluene.

17. The process according to claim 11, wherein the molar ratio of Lewis acid to the at least one lanthanide series compound is in the range of from 0.01:1 to 1:1.

18. The process according to claim 11, wherein the molar ratio of Lewis acid to the at least one lanthanide series compound is in the range of 0.05:1 to 0.5:1.

19. The process according to claim 11, wherein the at least one lanthanide series compound is represented by a formula selected from the group consisting of $Ln(R^1CO_2)_3$, $Ln(OR^1)_3$, $Ln(NR^1R^2)_3$, $Ln(SR^1)_3$, $Ln(-OPO(OR)_2)$, $Ln(-OSO_2(R))_3$, and $Ln(PR^1R^2)_3$, wherein Ln is a rare earth element in the lanthanide series having an atomic number of 57 to 71 and R, $R^1$ and $R^2$ are independently selected from alkyl, cycloalkyl and aryl hydrocarbon substituents having 1 to 20 carbon atoms.

20. The process according to claim 11, wherein the Lewis acid is $BBr_3$, $SnCl_4$, $ZnCl_2$, $MgCl_2$, or $MgBr_2 \cdot nEt_2O$.

21. The process according to claim 11, wherein the solution of the at least one lanthanide series compound in the inert solvent has a Brookfield viscosity of at least 1000 centipoise prior to the addition of the Lewis acid.

22. The process according to claim 11, wherein the solution of the at least one lanthanide series compound in the inert solvent has a Brookfield viscosity of less than 1000 centipoise after the addition of the Lewis acid.

23. A process for preparing a catalyst solution containing at least one lanthanide series compound consisting essentially of: the direct synthesis of the at least one lanthanide series compound in an inert solvent followed by the addition of a Lewis acid in an amount sufficient to form a solution having a Brookfield viscosity of less than 1000 centipoise after treatment with the Lewis acid.

24. A gel-free catalyst solution consisting essentially of: (a) a mixture of at least one lanthanide series compound having at least one rare earth element in the lanthanide series; (b) an inert solvent; (c) a Lewis acid, the Lewis acid selected from the group consisting of a transition metal halide, an organometallic halide whose metal is of group 2, 12, 13 and 14 of the Periodic System, and a halide of an element of group 2, 12, 13, 14 and 15 of the Periodic System, the Lewis acid being present in an amount sufficient to prevent gel formation of the at least one lanthanide series compound when mixed with the inert solvent; and (d) an organic magnesium compound of the formula $MgR^2R^3$ wherein $R^2$ and $R^3$ are the same or different and are hydrogen atoms or hydrocarbon substituents having 1 to 8 carbon atoms, excluding the case where $R^2$ and $R^3$ are both hydrogen atoms.

25. The solution according to claim 24, wherein the at least one rare earth element in the lanthanide series is lanthanum, cerium, praseodymium, neodymium, or mixtures thereof.

26. The solution according to claim 24, wherein the at least one rare earth element in the lanthanide series is a mixture of rare earth elements with atomic numbers from 57 to 71.

27. The solution according to claim 24, wherein the at least one rare earth element in the lanthanide series is a mixture of rare earth elements containing at least 10% by weight of at least one of lanthanum, cerium, praseodymium, or neodymium.

28. The solution according to claim 24, wherein the inert solvent comprises at least one of an aliphatic, cycloaliphatic, or aromatic solvent.

29. The solution according to claim 24, wherein the inert solvent comprises at least one of pentane, hexane, heptane, cyclohexane, benzene, or toluene.

30. The solution according to claim 24, wherein the molar ratio of Lewis acid to the at least one lanthanide series compound is in the range of from 0.005:1 to 5:1.

31. The solution according to claim 24, wherein the molar ratio of Lewis acid to the at least one lanthanide series compound is in the range of 0.05:1 to 0.5:1.

32. The solution according to claim 24, wherein the at least one lanthanide series compound is represented by a formula selected from the group consisting of $Ln(R^1CO_2)_3$, $Ln(OR^1)_3$, $Ln(NR^1R^2)_3$, $Ln(-OPO(OR)_2)$, $Ln(-OSO_2(R))_3$, $Ln(SR^1)_3$, and $Ln(PR^1R^2)_3$, wherein Ln is a rare earth element in the lanthanide series having an atomic number of 57 to 71 and R, $R^1$, and $R^2$ are independently selected from alkyl, cycloalkyl and aryl hydrocarbon substituents having 1 to 20 carbon atoms.

33. The solution according to claim 24, wherein the Lewis acid is $BBr_3$, $SnCl_4$, $ZnCl_2$, $MgCl_2$, or $MgBr_2 \cdot n\, Et_2O$.

* * * * *